US012761229B2

(12) United States Patent
Fraser

(10) Patent No.: US 12,761,229 B2
(45) Date of Patent: Oct. 13, 2026

(54) DIAGNOSTIC AND THERAPY OF TRAUMATIC BRAIN INJURY

(71) Applicant: LONDON HEALTH SCIENCES CENTRE RESEARCH INC., London (CA)

(72) Inventor: Douglas D. Fraser, London (CA)

(73) Assignee: London Health Sciences Centre Research Inc., London (CA)

( * ) Notice: Subject to any disclaimer, the term of this patent is extended or adjusted under 35 U.S.C. 154(b) by 642 days.

(21) Appl. No.: 18/033,029

(22) PCT Filed: Oct. 22, 2021

(86) PCT No.: PCT/CA2021/051493
§ 371 (c)(1),
(2) Date: Apr. 20, 2023

(87) PCT Pub. No.: WO2022/082318
PCT Pub. Date: Apr. 28, 2022

(65) Prior Publication Data

US 2023/0393153 A1 Dec. 7, 2023

Related U.S. Application Data

(60) Provisional application No. 63/104,680, filed on Oct. 23, 2020.

(51) Int. Cl.

| | |
|---|---|
| ***G01N 33/68*** | (2006.01) |
| ***A61K 38/17*** | (2006.01) |
| ***A61P 25/00*** | (2006.01) |

(52) U.S. Cl.
CPC ..... *G01N 33/6896* (2013.01); *A61K 38/1709* (2013.01); *A61P 25/00* (2018.01); *G01N 2800/52* (2013.01); *G01N 2800/60* (2013.01)

(58) Field of Classification Search
None
See application file for complete search history.

(56) References Cited

U.S. PATENT DOCUMENTS

2018/0074038 A1* 3/2018 Fraser .................. G01N 33/487
2023/0135030 A1* 5/2023 Rai ...................... G01N 33/534
435/7.1

OTHER PUBLICATIONS

Chen et al (Brain Research Bulletin, 163, 2000, 178-189) (Year: 2000).*
Kelner et al (The Journal of Biological Chemistry, 275(1), 2000, 580-584) (Year: 2000).*

* cited by examiner

*Primary Examiner* — Celeste A Roney
(74) *Attorney, Agent, or Firm* — Eduardo Krupnik

(57) ABSTRACT

A method of diagnosing and prognosticating an acquired central nervous system injury (ACNSI) in a subject that includes: (a) obtaining a test sample from the subject (b) comparing levels a biomarker in the test sample with known normal or abnormal reference levels of the biomarker. A change (increase or decrease) in the levels of the biomarker in the test sample relative to the known reference levels of the biomarker is indicative of ACNSI diagnosis in the subject, the biomarker being one or a combination of two or more of the proteins listed in Table 2. ACNSI includes concussion and primary blast in blast-induced traumatic brain injury.

18 Claims, 3 Drawing Sheets

DIAGNOSTIC AND THERAPY OF TRAUMATIC BRAIN INJURY

CROSS REFERENCE TO RELATED APPLICATIONS

This application is a national stage application under 35 U.S.C. 371 of International Application No. PCT/CA2021/051493, filed Oct. 22, 2021, which in turn claims the benefit under 35 U.S.C. 119(e) of U.S. Provisional Ser. No. 63/104,680, filed Oct. 23, 2020, the contents of each of which are hereby incorporated by reference into the present disclosure.

FIELD OF THE INVENTION

This invention relates to the diagnosis and treatment of traumatic brain injury.

BACKGROUND OF THE INVENTION

Acquired brain injury (ABI) and Acquired Spinal Cord Injury (ASI) are brain and spinal damage, respectively, caused by events that occur in utero, perinatal and post-natal. These impairments result from either traumatic brain injury (e.g., mechanical, pressure-wave, etc.) or non-traumatic injury derived from either an internal or external source (e.g., stroke, tumors, infection, poisoning, hypoxia, ischemia, radiation, substance abuse, etc.).

Traumatic brain injury (TBI) is an insult to the brain from an external mechanical force or blast, leading to permanent or temporary impairment of cognitive, physical, and psychosocial functions, with an associated diminished or altered state of consciousness (includes both concussion and blast injury). The Head Injury Interdisciplinary Special Interest Group of the American Congress of Rehabilitation Medicine defines "mild" TBI as "a traumatically induced physiologic disruption of brain function, as manifested by one of the following: any period of loss of consciousness (LOC), any loss of memory for events immediately before or after the event, any alteration in mental state at the time of the event and focal neurologic deficits, which may or may not be transient. The Glasgow Coma Scale (GCS) helps defines the severity of a TBI (3-8, severe; 9-12 moderate; 13-15 mild), based on eye, verbal and motor responses. TBI is a major public health concern of epidemic proportions, with an annual incidence of 1.6 to 3.2 million in the United States. Mild TBI or mTBI, of which mechanical trauma (includes concussion) and blast wave injury are subsets, is the most common form, representing nearly 75% of all TBIs [http://www.cdc.gov/TraumaticBrainInjury]. Mild TBI may be caused by impact forces in which the head strikes or is struck by something, o impulsive forces, in which the head moves without itself being subject to trauma (for example, when the chest hits something and the head snaps forward). All age groups suffer concussions, from the very young to the elderly. Certain activities are more frequently associated with concussions, including athletics and military service, but they also result from general trauma caused by motor vehicle collisions, falls from height and assaults. Concussions often result in significant acute symptoms and in some individuals, long-term neurological dysfunction.

A pressure-wave (e.g., bomb blast) may cause the full severity range of TBI, from mild to severe, and may include penetrating injury from projectiles. The pathophysiology of blast-related TBI is distinctive, with injury magnitude dependent on several factors, including blast energy and distance from the blast epicenter (31). A blast injury is a complex type of physical trauma resulting from direct or indirect exposure to an explosion (31). Primary injuries are caused by blast overpressure waves, or shock waves. These are especially likely when a person is close to an exploding munition, such as a land mine. Animal models suggest that the brain is vulnerable to primary blast injury. Shear and stress waves from the over-pressurization could potentially cause TBI directly (e.g., concussion, hemorrhage, edema, diffuse axonal injury). The primary blast mechanism can also result in cerebral infarction due to blast lung injury and consequent formation of gas emboli. ["Blast Injuries: Traumatic Brain Injuries from Explosions", Brainline.org]

While diagnosis of moderate to severe TBI is straightforward, mild TBI is under-diagnosed following concussion and explosive events ["Blast Injuries: Traumatic Brain Injuries from Explosions", Brainline.org]. That is, while moderate and severe TBI are easily diagnosed based on clinical signs, mild TBI can be missed due to subtle, transient or absent clinical signs. The latter require an objective diagnostic, such as a blood test that is sensitive, specific and reproducible.

Diagnosis of clinically significant mTBI can be difficult, as are the decisions to stop play or activities. It is also unclear when mTBI patients should return to daily activities. Thus, there is great interest in discovery of biomarkers to aid in mTBI, including primary brain blast injury and concussion diagnoses, prognoses and rehabilitation. At present, no single biomarker has sufficient sensitivity and specificity.

Non-traumatic brain injuries (non-TBI) can also result in mildly abnormal neurological symptoms. Given the often-subtle nature of non-TBI injuries, they could be better identified with an objective diagnostic test, such as a blood test, that is sensitive, specific and reproducible.

Traumatic spinal cord injuries (TSI; e.g. injuries from spine hyperflexion, hyperextension, lateral stress, rotation, compression, distraction and partial spinal cord transection; often from motor vehicle collisions, falls from height, sports, etc.) and non-traumatic spinal cord injuries (non-TSI; e.g, intervertebral disk disease, interruption of blood supply, infection, electrocution, cancer, radiation, etc) can also result in mild peripheral symptoms (e.g., an "incomplete" injury). Given the often-subtle nature of TSI and non-TSI injuries, they could be better identified with an objective diagnostic test, such as a blood test, that is sensitive, specific and reproducible.

Concussions remain a major global health care problem. (1) Approximately half of all adolescent concussions occur in sporting activities. (2, 3) Accurate diagnosis of concussion is essential to optimize medical care, to provide timely interventions and to prevent repeat injury prior to healing. Diagnosis of concussion relies on an injury event, which may be a direct blow to the head or as a result of transmitted forces from a blow to the body, as well as standardized clinical testing with concussion tools. (4) However, concussion diagnoses are often uncertain as self-reporting of symptoms can be inaccurate, (5) and the contribution of other factors, such as chronic pain, can exacerbate symptoms. (6)

Adolescents are particularly susceptible to concussions and to their potentially long-lasting neurological effects, (7, 8) making accurate diagnoses in this age group critically important. To date, neither a single nor cluster of symptoms accurately predict concussions in adolescents, although self-reported headache, head pressure, fatigue, and/or noise and light sensitivity have been identified as useful discriminators of injury. (9, 10) A number of blood protein and lipid biomarkers for concussion diagnoses have also been investigated; (4, 11-14) however, current concussion guidelines do not recommend the use of any blood biomarkers for diagnosis in children due to insufficient evidence,4, 15 illustrating the need for additional biomarker exploratory studies.

Novel protein biomarker identification using bodily fluids like blood, plasma and so forth is possible with antibody-, gel- and chromatography-based techniques. Proximity extension assay (PEA) is a relatively new form of targeted proteomics that combines protein-specific antibodies with unique deoxyribonucleic acid tags, followed by amplification with either quantitative polymerase chain reaction or next generation sequencing. [16, 17] The result is a targeted proteomic approach to biomarker discovery with excellent sensitivity and specificity over a broad dynamic range. Indeed, PEA offers a high level of precision, and is well suited for large-scale studies due to minimal matrix interference and cross reactivity. PEA has not yet been applied to biomarker(s) for mTBI.

SUMMARY OF THE INVENTION

In one embodiment, the present invention is a method of diagnosing an acquired central nervous system injury (ACNSI) in a subject comprising: (a) obtaining a biological sample from the subject and measuring levels of a biomarker in the biological sample, (b) comparing the levels of the biomarker in the biological sample with control reference levels of the biomarker, wherein a change in the levels of the biomarker in the biological sample relative to the control reference levels of the biomarker is indicative of a positive ACNSI diagnosis in the subject, the biomarker being one or combination of two or more of the proteins listed in Table 2.

In one embodiment of the method of diagnosing ACNSI in a subject of the present invention, the biomarker is one or a combination of two or more of ATOX1, SPARC, CD34, PQBP1, IGFBPL1 and/or NT5C3A.

In one embodiment of the method of diagnosing ACNSI in a subject of the present invention, the biomarker is a combination of ATOX1 and SPARC.

In one embodiment of the method of diagnosing ACNSI in a subject of the present invention, the biomarker is a combination of ATOX1, SPARC and NT5C3A.

In one embodiment of the method of diagnosing ACNSI in a subject of the present invention, the method further comprises (c) treating the subject for ACNSI only when there is a change in the levels of the biomarker in the biological sample relative to the control reference levels of the biomarker indicative of the positive ACNSI diagnosis of the subject.

In one embodiment of the method of diagnosing ACNSI in a subject of the present invention, the method further comprises obtaining recovery samples from the subject during the subject's treatment for ACNSI and measuring levels of the biomarker in the recovery samples, wherein an approximation in the levels of the biomarker in the recovery samples to the control reference levels is indicative of a normalization of the subject.

In one embodiment of the method of diagnosing ACNSI in a subject of the present invention, the control reference levels of the biomarker are derived from normal subjects or from ACNSI positive subjects.

In one embodiment of the method of diagnosing ACNSI in a subject of the present invention, the biomarker is selected based on an area under the curve receiver operating characteristic (AUC-ROC) analysis of the biomarker. In aspects, the AUC of the biomarker is 0.78 or more.

In one embodiment of the method of diagnosing ACNSI in a subject of the present invention, the biological sample is blood, blood plasma, blood serum, capillary blood, saliva, tear, sweat, synovial fluid, urine, spinal fluid, bronchoalveolar lavage, hippocampal tissue or ipsilateral cortex tissue and extracts.

In one embodiment of the method of diagnosing ACNSI in a subject of the present invention, the ACNSI is mild traumatic brain injury (mTBI), non-traumatic brain injury (non-TBI), mild traumatic spinal cord injury (mTSI) or non-traumatic spinal cord injury (non-TSI).

In one embodiment of the method of diagnosing ACNSI in a subject of the present invention, the ACNSI is concussion or primary blast in blast-induced traumatic brain injury.

In one embodiment of the method of diagnosing ACNSI in a subject of the present invention, the ACNSI is concussion.

In another embodiment, the present invention provides for a method of treating ACNSI in a subject, the method comprising administering to the subject an inhibitor or antagonist of NT5C3A.

In another embodiment, the present invention provides for a method of treating ACNSI, the method comprising administering to the subject one or a combination of ATOX1, SPARC, CD34, PQBP1, IGFBPL1, or their fragments, agonists or analogues.

In one embodiment of the methods of treating ACNSI of the present invention, the ACNSI is mild traumatic brain injury (mTBI), non-traumatic brain injury (non-TBI), mild traumatic spinal cord injury (mTSI) or non-traumatic spinal cord injury (non-TSI).

In another embodiment of the methods of treating ACNSI of the present invention, the ACNSI is concussion or primary blast in blast-induced traumatic brain injury.

In another embodiment of the methods of treating ACNSI of the present invention, the ACNSI is concussion.

In another embodiment, the present invention is a use of the level of a biomarker in a biological sample of a subject in the diagnosis of ACNSI, wherein the biomarker is one or a combination of two or more of the proteins listed in Table 2.

In one embodiment of the use of the level of a biomarker in a biological sample of a subject in the diagnosis of ACNSI, the biomarker is one or a combination of two or more of ATOX1, SPARC, CD34, PQBP1, IGFBPL1 and/or NT5C3A.

In another embodiment of the use of the level of a biomarker in a biological sample of a subject in the diagnosis of ACNSI, the biomarker is a combination of ATOX1 and SPARC.

In another embodiment of the use of the level of a biomarker in a biological sample of a subject in the diagnosis of ACNSI, the biomarker is a combination of ATOX1, SPARC and NT5C3A. In another embodiment of the use of the level of a biomarker in a biological sample of a subject in the diagnosis of ACNSI, the biological sample is blood, blood plasma, blood serum, capillary blood, saliva, tear, sweat, synovial fluid, urine, spinal fluid, bronchoalveolar lavage, hippocampal tissue or ipsilateral cortex tissue and extracts.

In another embodiment of the use of the level of a biomarker in a biological sample of a subject in the diagnosis of ACNSI, the ACNSI is mild traumatic brain injury (mTBI), non-traumatic brain injury (non-TBI), mild traumatic spinal cord injury (mTSI) or non-traumatic spinal cord injury (non-TSI).

In another embodiment of the use of the level of a biomarker in a biological sample of a subject in the diagnosis of ACNSI, the ACNSI is concussion or primary blast in blast-induced traumatic brain injury.

In another embodiment of the use of the level of a biomarker in a biological sample of a subject in the diagnosis of ACNSI, the ACNSI is concussion.

In another embodiment, the present invention relates to a use of a NT5C3A inhibitor or antagonist in the treatment of ACNSI in a subject.

In another embodiment, the present invention relates to a use of one or more of ATOX1, SPARC, CD34, PQBP1 and/or IGFBPL1, a fragment, an agonist or analogue thereof in the treatment of ACNSI in a subject.

In one embodiment of the present invention, the ACNSI is mild traumatic brain injury (mTBI), non-traumatic brain injury (non-TBI), mild traumatic spinal cord injury (mTSI) or non-traumatic spinal cord injury (non-TSI).

In another embodiment of the present invention, the ACNSI is concussion or primary blast in blast-induced traumatic brain injury.

In another embodiment of the present invention, the ACNSI is concussion.

In another embodiment, the present invention relates to an ACNSI diagnostic apparatus, the ACNSI diagnostic apparatus including a non-transitory computer readable storage medium storing computer-executable instructions that when executed by a computer control the computer for performing a method of diagnosing ACNSI in a subject, said executable instructions comprising: (a) comparing levels of a biomarker in a biological sample of the subject, with control reference levels of the biomarker, and (b) providing a ACNSI positive signal when there is a change in the levels of the biomarker the biological sample relative to the control reference levels of the biomarker, the biomarker being one or a combination of two or more of the proteins listed in Table 2.

In one embodiment of ACNSI diagnostic apparatus of the present invention, the biomarker is one or a combination of two or more of ATOX1, SPARC, CD34, PQBP1, IGFBPL1 and/or NT5C3A.

In another embodiment of ACNSI diagnostic apparatus of the present invention, the biomarker is a combination of ATOX1 and SPARC.

In another embodiment of ACNSI diagnostic apparatus of the present invention, the biomarker is a combination of ATOX1, SPARC and NT5C3A.

In another embodiment of ACNSI diagnostic apparatus of the present invention, the instructions further include comparing the levels of the biomarker in the test sample, with the levels of the biomarker in a sample obtained from the subject during the subject's treatment of ACNSI, wherein an increase or decrease in the level of biomarker during the treatment relative to the levels of the biomarker in the test ample as the case may be is indicative of a normalization of the subject.

In another embodiment of ACNSI diagnostic apparatus of the present invention, the biological sample is blood, blood plasma, blood serum, capillary blood, saliva, tear, sweat, synovial fluid, urine, spinal fluid, bronchoalveolar lavage, hippocampal tissue or ipsilateral cortex tissue and extracts.

In another embodiment of ACNSI diagnostic apparatus of the present invention, the ACNSI is mild traumatic brain injury (mTBI), non-traumatic brain injury (non-TBI), mild traumatic spinal cord injury (mTSI) or non-traumatic spinal cord injury (non-TSI).

In another embodiment of ACNSI diagnostic apparatus of the present invention, the ACNSI is concussion or primary blast in blast-induced traumatic brain injury.

In another embodiment of ACNSI diagnostic apparatus of the present invention, the ACNSI is concussion.

The present invention, in another embodiment, provides for a method of diagnosing an acquired central nervous system injury (ACNSI) in a subject comprising: (a) obtaining a proteomic profile from the subject; and (b) using multivariate statistical analysis and machine learning to compare the subject's profile with a predetermined set of metabolite profiles of ACNSI and a predetermined set of metabolite profiles of non-ACNSI (referred to as "control" or "normal") to determine if the subject has ACNSI, wherein the proteomic profile includes one or combination of two or more of the proteins listed in Table 2. In one embodiment, the proteomic profile is obtained from blood, blood plasma, blood serum, capillary blood, saliva, tear, sweat, synovial fluid, urine, spinal fluid, bronchoalveolar lavage, hippocampal tissue and/or ipsilateral cortex tissue and extracts.

In another embodiment, the present invention provides for a method of determining recovery of a subject undergoing ACNSI therapy, the method comprising: (a) obtaining a biological sample from the subject at different stages during the ACNSI therapy; and (b) comparing levels of a biomarker in the biological sample at each of the different stages with known normal reference levels of the biomarker, wherein a normalization of the levels of the biomarker in the biological sample at each subsequent stage relative to the known normal reference levels of the biomarker is indicative of the subject undergoing recovery ACNSI, the biomarker being one or combination of two or more of the proteins listed in Table 2. In embodiments, the biological sample is blood, blood plasma, blood serum, capillary blood, saliva, tear, sweat, synovial fluid, urine, spinal fluid, bronchoalveolar lavage, hippocampal tissue or ipsilateral cortex tissue and extracts.

In embodiments of the present invention the biomarker is one or a combination of two or more of ATOX1, SPARC, CD34, PQBP1, IGFBPL1 and/or NT5C3A.

In embodiments of the present invention the biomarker is detected using an immunoassay.

In embodiments of the present invention the immunoassay is an ELISA, Western blotting, Luminex bead-based assays, planar multiplex. assays, electrochemiluminescence, proximal extension assay (PEA) with oligonucleotide-labeled antibodies, lateral flow assay, RIA or Genome-wide location analysis (ChIP-Chip).

In embodiments of the present invention the biomarker is detected using mass spectrometry.

In embodiments of the present invention the ACNSI is mild traumatic brain injury (mTBI), non-traumatic brain injury (non-TBI), mild traumatic spinal cord injury (mTSI) or non-traumatic spinal cord injury (non-TSI).

In embodiments of the present invention the ACNSI is concussion or primary blast in blast-induced traumatic brain injury.

In embodiments of the present invention the ACNSI is concussion.

In another embodiment, the present invention relates to a method of prognosticating the duration of an ACNSI therapy in a patient and to determine when the patient has normalized, the method comprising following the levels of one or a combination of two or more of the proteins listed in Table 2 at different stages throughout the therapeutic treatment of the patient and comparing the levels of the one or more proteins at each of the different stages to known normal reference levels of the one or more proteins.

In another embodiment, the present invention provides for a method of detecting one or more of the proteins listed in Table 2 comprising detecting whether the one or more proteins are present in a biological sample collected from a subject suspected of having ACNSI by contacting the biological sample with an antibody against said protein and detecting binding of the antibody to the protein.

BRIEF DESCRIPTION OF THE DRAWINGS

The following figures illustrate various aspects and preferred and alternative embodiments of the invention.

DESCRIPTION OF THE INVENTION

Abbreviations

Figure 1A:
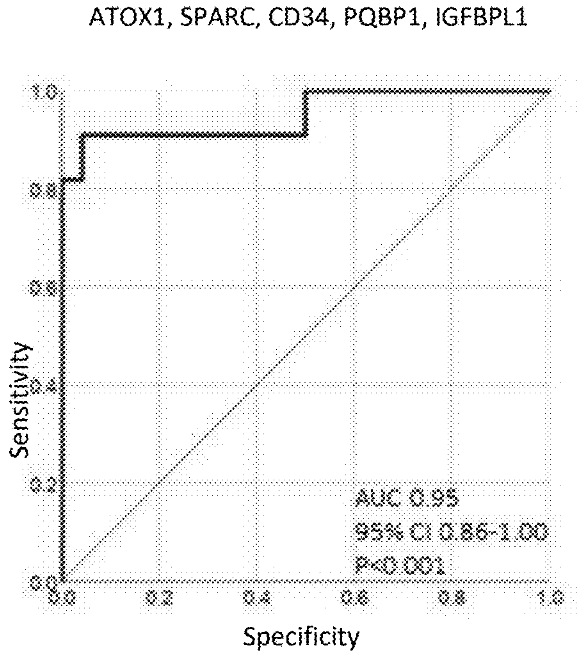
FIGS. 1A-1E: Receiver operating characteristic (ROC) curve analyses of a protein combination and several protein ratios for concussion diagnosis. (1A) A final ROC curve analysis for a combination of the top 5 proteins identified (ATOX1, AUC 0.81, P<0.003; SPARC, AUC 0.81, P=0.004; CD34, AUC 0.79, P=0.006; PQBP1, AUC 0.78, P=0.008; and IGFBPL1, AUC 0.78, P=0.008). (1B) A final ROC curve analysis for a ratio between NT5C3A/SPARC. (1C) A final ROC curve analysis for a ratio NT5C3/ATOX1. (1D) A final ROC curve analysis for a combination of SPARC and ATOX1. (1E) A final ROC curve analysis for a combination of NT5C3A, ATOX1 and SPARC. The AUC, 95% confidence intervals (CIs) and P-value are indicated. The solid line reflects an AUC of 0.5 attributed to chance.

Unless defined otherwise, all technical and scientific terms used herein have the same meaning as commonly understood by one of ordinary skill in the art to which this invention belongs. Also, unless indicated otherwise, except within the claims, the use of “or” includes “and” and vice versa. Non-limiting terms are not to be construed as limiting unless expressly stated or the context clearly indicates otherwise (for example “including”, “having” and “comprising” typically indicate “including without limitation”). Singular forms including in the claims such as “a”, “an” and “the” include the plural reference unless expressly stated otherwise. “Consisting essentially of” means any recited elements are necessarily included, elements that would materially affect the basic and novel characteristics of the listed elements are excluded, and other elements may optionally be included. “Consisting of” means that all elements other than those listed are excluded. Embodiments defined by each of these terms are within the scope of this invention.

The contents of all documents (including patent documents and non-patent literature) cited in this application are incorporated herein by reference.

All numerical designations, e.g., levels, amounts and concentrations, including ranges, are approximations that typically may be varied (+) or (−) by increments of 0.1, 1.0, or 10.0, as appropriate. All numerical designations may be understood as preceded by the term “about”.

In this document the definition of “mild traumatic brain injury” “mTBT””, which may also be referred to in the literature as mild head injury or concussion, is that taken from the American Congress of Rehabilitation Medicine (ACRM; J Head Trauma Rehabil 1993;8 (3): 86-87), and it refers to a person who has had a traumatically induced physiological disruption of brain function, as manifested by at least one of the following: 1. any period of loss of consciousness; 2. any loss of memory for events immediately before or after the event; 3. any alteration in mental state at the time of the event (eg, feeling dazed, disoriented, or confused); and 4. focal neurological deficit(s) that may or may not be transient; but where the severity of the injury does not exceed the following: loss of consciousness of approximately 30 minutes or less; after 30 minutes, an initial Glasgow Coma Scale (GCS) of 13-15; and posttraumatic amnesia (PTA) not greater than 24 hours. This definition includes: 1. the head being struck, 2. the head striking an object, and 3. the brain undergoing an acceleration/deceleration movement (i.e., whiplash) without direct external trauma to the head. Computed tomography, magnetic resonance imaging, electroencephalogram, near infrared spectroscopy, positive emission tomography or routine neurological evaluations may be normal. Due to the lack of medical emergency, or the realities of certain medical systems, some patients may not have the above factors medically documented in the acute stage. In such cases, it is appropriate to consider symptomatology that, when linked to a traumatic head injury, can suggest the existence of a mTBI. mTBI includes, as non-limiting examples, traumatic mechanical injuries such as concussion and blast injury.

“Non-traumatic brain injuries” (non-TBI) include brain injuries that may be the result of strokes, poisonings, psychological distresses, chemicals, infections, inflammation, autoimmune diseases, degenerative processes, hypoxia, ischemia, metabolic derangements and cancer/radiation.

In this document the definition of “mild traumatic spinal cord injury” “mTSI” is an incomplete injury with one or more spinal symptoms that may resolve over time (e.g. loss of bowel or bladder control, poor regulation of blood pressure and body temperature, pain, poor sensation, poor sense of body position, sexual dysfunction, etc.). Causes of mTSI may include contusion, stretch and partial cord transection.

“Non-traumatic spinal cord injuries” (non-TSI) include spinal cord injuries that may be the result of strokes, poisonings, chemicals, infections, inflammation, autoimmune diseases, degenerative processes, hypoxia, ischemia, metabolic derangements and cancer/radiation.

“Metabolome” refers to the collection of all metabolites in a biological cell, tissue, organ or organism, which are the end products of cellular processes. “Metabolome” includes lipidome, sugars, nucleotides and amino acids. Lipidome is the complete lipid profile in a biological cell, tissue, organ or organism.

“Metabolomic profiling” refers to the characterization and/or measurement of the small molecule metabolites in biological specimen or sample, including cells, tissue, organs, organisms, or any derivative fraction thereof and fluids such as blood, blood plasma, blood serum, capillary blood, saliva, synovial fluid, spinal fluids, urine, bronchoalveolar lavage, tissue extracts and so forth.

The metabolite profile may include information such as the quantity and/or type of small molecules present in the sample. The ordinarily skilled artisan would know that the information which is necessary and/or sufficient will vary depending on the intended use of the "metabolite profile." For example, the "metabolite profile," can be determined using a single technique for an intended use but may require the use of several different techniques for another intended use depending on such factors as the disease state involved, the types of small molecules present in a particular targeted cellular compartment, the cellular compartment being assayed per se, and so forth.

The relevant information in a "metabolite profile" may also vary depending on the intended use of the compiled information, e.g. spectrum. For example, for some intended uses, the amounts of a particular metabolite or a particular class of metabolite may be relevant, but for other uses the distribution of types of metabolites may be relevant.

Metabolite profiles may be generated by several methods, e.g., HPLC, thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarization interferometry, computational methods, liquid chromatography (LC) Light Scattering analysis (LS), gas chromatography (GC), or GC coupled with MS, direct injection (DI) coupled with LC-MS/MS and/or other methods or combination of methods known in the art.

The term "subject" as used herein refers all members of the animal kingdom including mammals, preferably humans.

The term "patient" as used herein refers to a subject that is suspected of having an acquired injury of the central nervous system (ACNSI). In this document ACNSI includes an acquired brain injury (ABI) and an acquired spinal cord injury (ASI). These injuries may be traumatic (mTBI and mTSI) and non-traumatic (non-TBI and non-TSI). mTBI includes concussion and blast, including blast overpressure wave injury. Non-TBI includes electrical-induced brain injury (electrocution), seizure-induced brain injury, surgical-induced brain injury, stroke-induced brain injury, poison-induced brain injury, psychological brain injury, chemical brain injury, infectious brain injury, ischemic brain injury, metabolic brain injury, inflammatory brain injury, autoimmune brain injury, degenerative brain injury, hypoxic brain injury, and cancer/radiation-induced brain injury. mTSI includes spinal cord contusion, stretch and/or partial transection, and the non-TSI includes intervertebral disk disease, electrical, stroke, poisoning, chemical, infectious, ischemia, metabolic, inflammatory, autoimmune, degenerative, hypoxic, and cancer/radiation-induced spinal cord injuries.

The term "proteome" is used herein to describe a significant portion of proteins in a biological sample at a given time. The concept of proteome is fundamentally different from the genome. While the genome is virtually static, the proteome continually changes in response to internal and external events.

The term "proteomic profile" is used to refer to a representation of the expression pattern of a plurality of proteins in a biological sample, e.g. a biological fluid at a given time. The proteomic profile can, for example, be represented as a mass spectrum, but other representations based on any physicochemical or biochemical properties of the proteins are also included. Thus the proteomic profile may, for example, be based on differences in the electrophoretic properties of proteins, as determined by two-dimensional gel electrophoresis, e.g. by 2-D PAGE, and can be represented, e.g. as a plurality of spots in a two-dimensional electrophoresis gel. Proteins can be measured with antibody tests (i.e. Western blotting, Luminex bead-based assays, planar multiplex assays, electrochemiluminescence, proximal extension assay (PEA) with oligonucleotide-labeled antibodies, ELISA, lateral flow assay and RIA as well as Genome-wide location analysis, also known as ChIP-Chip, which combines chromatin immunoprecipitation and DNA microarray analysis to identify protein-DNA interactions that occur in living cells), flow cytometry or mass spec techniques. Enzymes can be measured with enzyme assays that measure either the consumption of a substrate or production of product over time. Differential expression profiles may have important diagnostic value, even in the absence of specifically identified proteins. Single protein spots can then be detected, for example, by immunoblotting, multiple spots or proteins using protein microarrays. The proteomic profile typically represents or contains information that could range from a few peaks to a complex profile representing 50 or more peaks. Thus, for example, the proteomic profile may contain or represent at least 2, or at least 5 or at least 10 or at least 15, or at least 20, or at least 25, or at least 30, or at least 35, or at least 40, or at least 45, or at least 50, or at least 100 proteins.

Overview

The present disclosure relates to the use of proteomics, or the use of one biomarker or a cohort (group, or combination of two or more, or multiple) of biomarkers to diagnose, treat and follow up the recovery of acquired central nervous system injuries (ACNSI), including ABI and ASI. ABI includes mTBI and non-TBI. ASI includes mTSI and non-TSI. Traumatic injuries to the brain and spinal cord may include concussion and blast, including blast overpressure wave injury as well as spinal cord contusion, stretch and/or partial transection. Non-traumatic injuries (non-TBI and non-TSI) may include electrical-induced (electrocution), seizure-induced, surgical-induced, strokes, poisonings, psychological distresses, chemicals, infections, inflammation, autoimmune diseases, degenerative processes, hypoxia, ischemia, metabolic derangements and cancer/radiation (also, intervertebral disk disease for non-TSI). The present invention relates also to individual biomarkers in diagnosing ABI such as mTBI and non-TBI, and ASI, such as mTSI and non-TSI in a subject.

The biomarkers of the present invention can serve as therapeutic targets for the treatment of ACNSI and to follow up the recovery of ACNSI. In one embodiment, the biomarker is one or a combination of two or more of the proteins listed in Table 2. In another embodiment, the biomarker is one or more of ATOX1, SPARC, CD34, PQBP1, IGFBPL1 and/or NT5C3A.

In one embodiment, the present invention involves comparing the levels of a single biomarker or a combination of two or more of biomarkers in a subject's sample, such as blood, blood plasma, blood serum, capillary blood, saliva, synovial fluid, urine, tear, sweat, spinal fluid, bronchoalveolar lavage and extracts (for example extracts of hippocampal tissue or ipsilateral cortex tissue), using quantitative measurements of said biomarker or cohort of biomarkers to the levels of said single biomarker or cohort of biomarker in a known reference range, or in a normal population. A change, such as an increase or a decrease, in the level of the at least one biomarker in the subject's sample relative to the known reference or normal population being indicative of the subject having ACNSI.

The methods, apparatuses and computer programs of the present invention may be used in point-of-care metabolomics testing with portable, table/countertop or hand-held instruments that generate metabolite profiles.

In one embodiment, the one or more biomarkers are those listed in Tables 2.

In one embodiment of the present invention, the one or more biomarkers of the present invention are ATOX1, SPARC, CD34, PQBP1, IGFBPL1 and/or NT5C3A.

Since metabolites exist in a very broad range of concentrations and exhibit chemical diversity, there is no one instrument that can reliably measure all of the metabolites in the non-human or human metabolome in a single analysis. Instead, practitioners of metabolomic profiling generally use a suite of instruments, most often involving different combinations of liquid chromatography (LC) or gas chromatography (GC) coupled with MS, to obtain broad metabolic coverage [Circulation. 2012; 126:1110-1120] Other instruments such as electrochemical analysis, RI, UV, near-IR, LS, GC and so forth may also be used.

Point-of-care testing (e.g. hand held or table top antibody testing or MS) could be developed to identify ACNSI patients, and to prognosticate outcome and/or stratify to treatment.

As such, in one embodiment, the present disclosure provides for a method of diagnosing or prognosticating ACNSI in a subject, including acquired brain injury (ABI) and acquired spinal cord injuries (ASI). The method, in one embodiment, includes: (a) obtaining a test sample from the subject, (b) comparing levels of a biomarker in the biological sample with known control (normal or abnormal reference) levels of the biomarker, wherein a change (an increase or decrease) in the level of the biomarker in the test sample relative to the known control levels of the biomarker is indicative of ACNSI diagnosis in the subject, the biomarker being one or combination of two or more of the proteins listed in Table 2. In aspects, the biomarker being one or more of ATOX1, SPARC, CD34, PQBP1, IGFBPL1 and/or NT5C3A.

In embodiments of the invention, only in the case of a positive diagnosis, the method further comprises treating the subject for ACNSI.

In another embodiment, the method of diagnosing or prognosticating includes (a) obtaining a proteomic profile from the subject; and (b) using multivariate statistical analysis and machine learning to compare the subject's proteomic profile with a predetermined set of proteomic profiles of ACNSI injuries or infections and a predetermined set of metabolite profiles of non-ACNSI (referred to as "control" or "normal") to determine or diagnose if the patient has ACNSI injury or infection or prognosticate the ACNSI injury or infection. In one aspect, the proteomic profile includes one or a combination of two or more of the proteins listed in Table 2. In another aspect, the proteomic profile consists of one or a combination of two or more of the proteins listed in Table 2. In another aspect the proteomic profile comprises or consist of one or a combination of two or more of ATOX1, SPARC, CD34, PQBP1, IGFBPL1 and/or NT5C3A.

A library of the measurements of the biomarkers of the present invention may be established for diagnosed ACNSI cases. This library may be used as the predetermined, control set of biomarker measurements of ACNSI. Similarly, a predetermined set of normal biomarker measurements may be obtained from subjects known not to have ACNSI. A comparison may be made of the patient's biomarker's measurements, the predetermined biomarker measurements of ACNSI and the predetermined biomarker measurements of normal or control samples to determine not only if the patient has ACNSI but also the prognosis.

The libraries of predetermined biomarker measurements may be provided in a computer product (memory sticks, as an app for hand-held devices such as pads and cellular phones and so forth), or they may be uploaded to the memory of a computer system, including main frames, desktops, lab tops, handheld devices such as pads and cellular phones. The test sample or biological sample include blood or any other bodily fluid, for example whole blood, blood plasma, blood serum, capillary blood sample, saliva, synovial fluid, urine, spinal fluid, bronchoalveolar lavage, tears, sweat, extracts and so forth, may be taken from a patient. Biomarker measurements may be obtained from the patient's sample using any known technology (for example, high performance liquid chromatography, thin layer chromatography, electrochemical analysis, mass spectroscopy (MS), refractive index spectroscopy, ultra-violet spectroscopy, fluorescent analysis, radiochemical analysis, near-infrared spectroscopy, light scattering analysis, gas chromatography (GC), or GC coupled with MS, direct injection (DI) coupled with LC-MS/MS and so forth). The patient's biomarker measurements may then be uploaded to the computer system (main frames, desktops, lab tops, handheld devices and so forth). An operator may then compare the patient's biomarker measurements with the predetermined set of biomarker measurements of ACNSI and/or the predetermined biomarker measurements of a control or normal to determine not only if the patient has ACNSI, but also the prognosis, or whether a treatment is efficient.

Returns to a normal level of the biomarkers may serve as an aid in following medical interventions of individuals affected by ACNSI.

Therapies

By "inhibitor" is meant any molecule that inhibits, suppresses or causes the cessation of at least one biological activity of a biomarker of the present invention, e.g. by reducing, interfering with, blocking, or otherwise preventing the interaction or binding of the biomarker to its natural target. Inhibitors include low molecular weight antagonists, antibodies, proteins, peptides or ligands that impair the biological action of the biomarker, antisense oligonucleotides, including anti-sense RNA molecules and anti-sense DNA molecules that are complimentary to a nucleic acid sequence from a gene or genes that encode the biomarker may be used in the methods of the present invention to block the translation of mRNA and inhibit protein synthesis, or increasing mRNA degradation, thus decreasing the level of biomarker protein, and thus activity, in a cell. Small inhibitory RNA (siRNA) is a form of gene silencing triggered by double-stranded RNA (dsRNA). In siRNA sequence-specific, post-transcriptional gene silencing in animals and plants may be initiated by double-stranded RNA (dsRNA) that is homologous in sequence to the silenced gene. A siRNA (small interfering RNA) is designed to target and thus to degrade a desired mRNA (in this case encoding mRNA of a suitable biomarker of the present invention) in order not to express the encoded protein.

Ribozymes may also function as inhibitors of protein expression for use in the present invention. Ribozymes are enzymatic RNA molecules capable of catalyzing the specific cleavage of RNA.

This invention provides a method for treating ACNSI in a subject by administering to the subject one or more inhibitors of one or more of the biomarkers of the present invention that have elevated levels relative to a known normal standard, alone or in combination with a second agent. For example, the levels of NT5C3A have been found to be elevated relative to the control subjects. One or more inhibitors of NT5SC3A can be administered to a subject having ACNSI. The inhibitors may be formulated for oral administration, for administration by injection, for topical administration, inhalation.

This invention provides a method for treating ACNSI in a subject by administering to the subject the one or more biomarkers of the present invention that have decreased levels relative to a known normal standard, alone or in combination with a second agent. For example, the levels of ATOX1 have been found to be decreased relative to the control subjects. ATOX1 can be administered to a subject having ACNSI. ATOX1 may be formulated for oral administration, for administration by injection, for topical administration, inhalation. ATOX1 is a copper transporter. Thus, ATOX1 with or without copper can be administered. In one embodiment, the present invention is the use of ATOX1 to treat ACNSI in a subject. In another embodiment, the present invention is the use of ATOX1 in the manufacture of a medicament to treat ACNSI in a subject.

The one or more biomarker(s) of the present invention may be used to prognosticate the duration of the ACNSI therapy and to determine when a patient has normalized. This can be done by following the levels of one or more of the proteins listed in Table 2 throughout the therapeutic treatment of the patient. Patients may suffer serious outcomes from withdrawal of care after there has been no improvement in in their ACNSI. These biomarkers help determine who will have a bad outcome earlier and aid end of life decision making, or determine whom will do well and guide persistent management of the ACNSI. For example a concussed brain is in a vulnerable state that places it at increased risk of more debilitating injury should more trauma occur before metabolic homeostasis is restored. Accordingly, the present invention provides for a method of determining when metabolic homeostasis may have been restored in a patient who suffered ACNSI.

In another embodiment, the present invention provides for a computer program product for use in conjunction with a computer system. An ACNSI diagnostic apparatus, the ACNSI diagnostic apparatus including a non-transitory computer readable storage medium and a computer program mechanism embedded therein, the computer program mechanism comprising executable instructions for performing a method of diagnosing ACNSI in a subject, said executable instructions comprising: (a) comparing levels of a biomarker in a test sample of the subject, with control reference levels of the biomarker, and (b) providing a ACNSI positive signal (an output) when there is a change in the level of the biomarker the test sample relative to the control reference levels of the biomarker, the biomarker being one or a combination of two or more of the proteins listed in Table 2. In aspects, the biomarker being one or more of ATOX1, SPARC, CD34, PQBP1, IGFBPL1 and/or NT5C3A.

In another embodiment, the present invention provides for a non-transitory computer readable storage medium comprising executable instructions that when executed by a computer, control the computer for performing a method of diagnosing ACNSI in a subject, said executable instructions comprising: (a) comparing levels of a biomarker in a test sample of the subject, with control reference levels of the biomarker, and (b) providing a ACNSI positive signal (an output) when there is a change in the level of the biomarker the test sample relative to the control reference levels of the biomarker, the biomarker being one or a combination of two or more of the proteins listed in Table 2. In aspects, the biomarker being one or more of ATOX1, SPARC, CD34, PQBP1, IGFBPL1 and/or NT5C3A.

In order to aid in the understanding and preparation of the within invention, the following illustrative, non-limiting, examples are provided.

EXAMPLES

Example 1

Methods

This study was approved by Western University Human Ethics Review Board. Male adolescent ice hockey athletes (Bantam Division; aged 12-14 years) participated in this study. Patients suspected to have suffered a concussion were clinically evaluated at our academic Sports Medicine Clinic within 72 hours of the injury; a time frame to account for weekend injuries. They were either referred by other Health Care providers, including emergency physicians, family physicians, coaches and/or trainers, or they had booked an appointment by self-referral. Control patients were recruited via posters in hockey arenas or by coaches and/or trainers whom provided athletes and their families with a study information package. To be considered as controls, the athletes were non-injured hockey players that were age- and sex-matched, and that had not suffered a diagnosed concussion in the past 6 months. All patients with a suspected concussion, as well as non-injured control athletes, including their parents/guardians, completed a Sports Concussion Assessment Tool-3$^{rd}$ Edition (SCAT3;[18] 13-14 years of age). A complete history, physical and neurologic examination were also conducted by an experienced sport medicine physician. All prescription medications were recorded. Our patient evaluation was in keeping with the Berlin Consensus guidelines.[4] Any subject with a reported neurological disease was excluded. All injured athletes were provided with standardized concussion care.

All athletes on their first clinic visit had 20 ml of blood drawn into EDTA Vacutainer tubes. No restrictions were placed on the time-of-day collection by intent and design, to better represent the natural state of the athlete. The blood was centrifuged, the plasma aliquoted into cryovials at a volume of 500 μl and stored at −80° C. Freeze/thaw cycles were avoided. Plasma was collected by strict standard operating procedures, with equal processing times between cohorts.

A total of 1,472 plasma proteins were measured using an immunoassay based on PEA technology (Olink Proteomics, Sweden). A 0.25 mL aliquot of trisodium citrate anticoagulated plasma was obtained from each subject and was transported frozen on dry ice to the Olink (Boston, MA). The data generated were expressed as relative quantification on the log 2 scale of normalized protein expression (NPX) values. Individual samples were screened based on quality controls for immunoassay and detection, as well as degree of hemolysis. NPX values were rank-based normal transformed for further analyses. Following proteomic quality control, all 35 participants were deemed suitable for analysis.

Demographic data, concussion tool data and protein concentrations were reported as median (interquartile range [IQR]). Statistical significance for demographic data was determined with P-values<0.05. A P-value<0.05 was used as our standard of statistical significance when comparing protein concentrations by intent and design, and recognizing the theoretical risk of false positives. Receiver operating characteristic (ROC) curves were conducted to determine sensitivity and specificity of all individual proteins for predicting concussion. Area-under-the-curve (AUC) was calculated for each protein, with an AUC>0.7 considered as acceptable.[19] The coordinates of the curves were then analyzed to identify cut-off values based on the highest sensitivity and specificity for predicting concussion. Logistic regression analyses were also conducted with concussion as the outcome and combinations or ratios of the top six proteins with AUC>0.78 entered as predictors; the predicted values from the logistic regression models were then saved for use in ROC curve analyses to determine the most parsimonious combination of proteins with the greatest combined AUC. All: analyses were conducted using SPSS version 25 (IBM Corp., Armonk, NY, USA).

Results

Subject demographic and injury data are presented in Table 1. We investigated a total of 11 concussed athletes (median years of age 13; IQR 13, 14) and 24 age-, sex- and activity-matched athlete control subjects (median years of age 13, IQR 12.3, 14; P=0.406). The predominant mechanism of injury was a body check. One concussion patient had brief loss of consciousness, whereas 4 concussion patients reported amnesia. Headache was the most prevalent self-reported symptom, occurring in 91% of concussion patients. Self-reported symptom evaluation as per SCAT3 (n=11) revealed a median total symptom score and a median total symptom severity of 13 (IQR 7, 16) and 25 (IQR 12, 49), respectively. In contrast, the non-concussed athletes had a median total symptom score and a median total symptom severity of 0 (IQR 0, 0). All concussed adolescent athletes underwent brain multiparametric magnetic resonance imaging, 19 which demonstrated diffusion abnormalities within multiple white matter tracts and functional hyper-connectivity, thereby confirming concussion status.

Medical and medication history are also reported in Table 1. Three concussion patients reported at least one previous concussion, while 6 control subjects had suffered previous concussions (P=1.000). There were no significant differences between groups with respect to anxiety, depression, mood disorders or other pre-existing medical conditions. Three concussion patients were prescribed medications, including salbutamol, methylphenidate and fluoxetine, while 4 control subjects had been prescribed medications, including salbutamol, methylphenidate, cetirizine and loratadine (P=0.279). None of the patients had been prescribed anti-inflammatoires or analgesics.

Figure 1B:
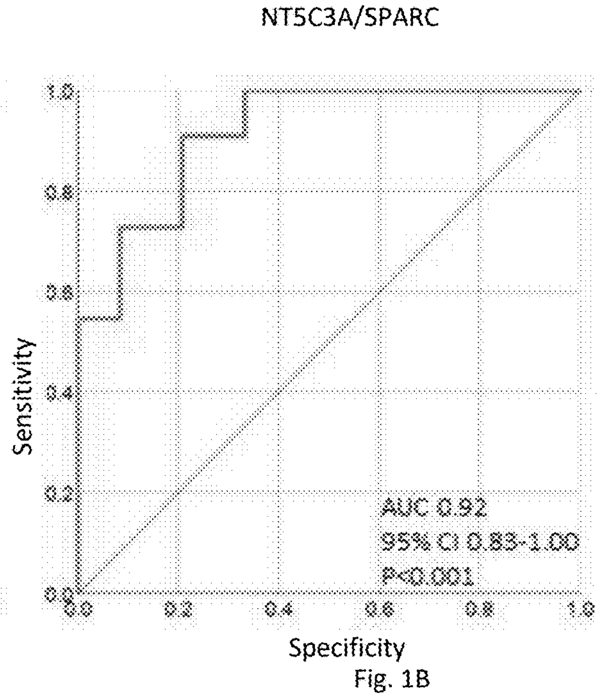
Figure 1C:
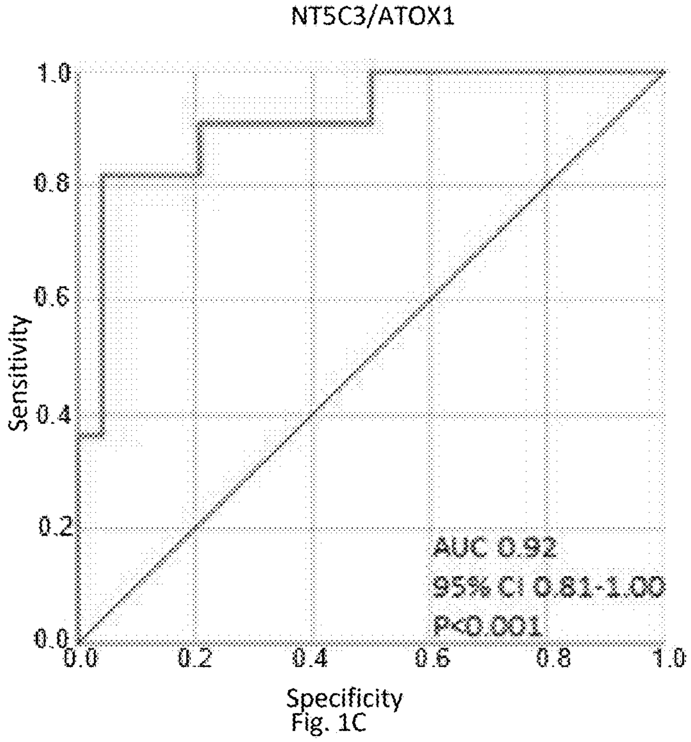
Figure 1D:
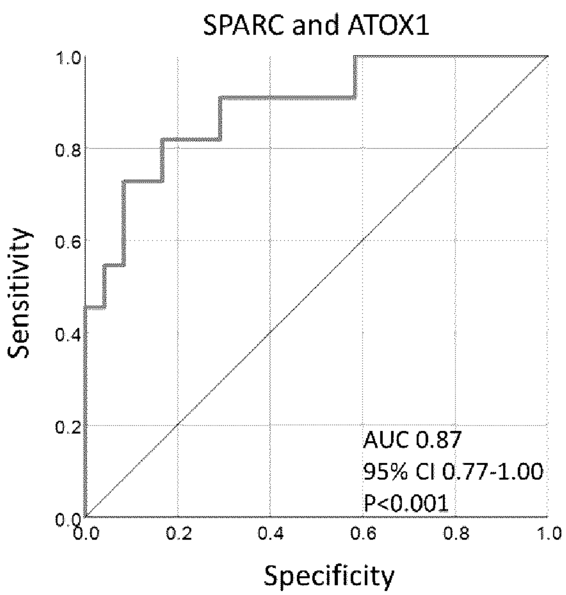
Figure 1E:
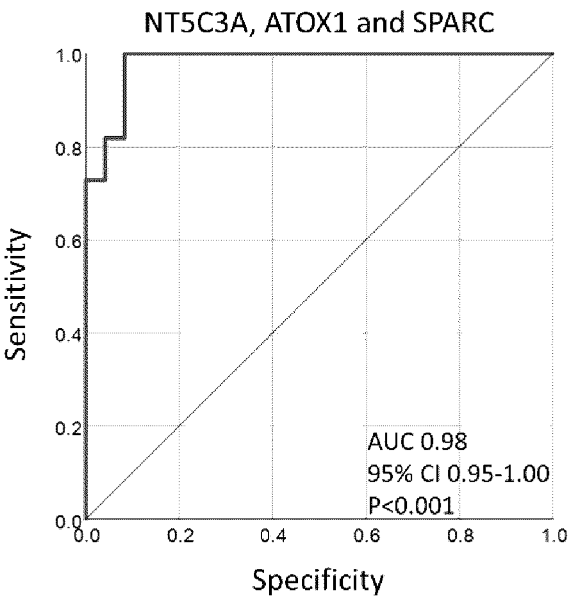

The median time from concussion occurrence to blood draw at the first clinic visit was 2.0 days (IQR 1, 3). We then examined 1,472 plasma proteins, of which 92 had a statistically significant change in concentration after concussion (P<0.05; Table 2). Of the 92 proteins that changed significantly, 78 proteins decreased in concentration, while 14 proteins increased in concentration. A ROC curve analysis was completed for each of the 92 proteins; the top 6 proteins with an AUC≥0.78 were used in combination (FIGS. 1A, 1D and 1E) or ratio modeling (FIGS. 1B and 1C). The AUCs and cut off values were: ATOX1 0.81 and <0.52 (P=0.003); SPARC 0.81 and <0.56 (P=0.004); CD34 0.79 and <0.62 (P=0.006); PQBP1 0.78 and <0.58 (P=0.008); IGFBPL1 0.78 and <0.46 (P=0.008); and NT5C3A 0.78 and >0.90 (P=0.009). When the predicted values for the top 2 proteins SPARC and ATOX1, as determined by regression analyses, were combined, the AUC increased to 0.87 (FIG. 1D). When the predicted values for the top 5 proteins (ATOX1, SPARC, CD34, PQBP1 and IGFBPL1), as determined by regression analyses, were combined, the AUC increased to 0.95 (FIG. 1A; P<0.001; 95% CI 0.86-1.00). When the predicted values of NT5C3A, ATOX1 and SPARC were combined, the AUC increased to 0.98 (FIG. 1E). Two protein ratios were also determined that provided an AUC of 0.92; NT5C3A/SPARC (FIG. 1B; P<0.001; 95% CI 0.83, 1.00) and NT5C3A/ATOX1 (FIG. 1C; P<0.001; 95% CI 0.81, 1.00).

Figure 2A:
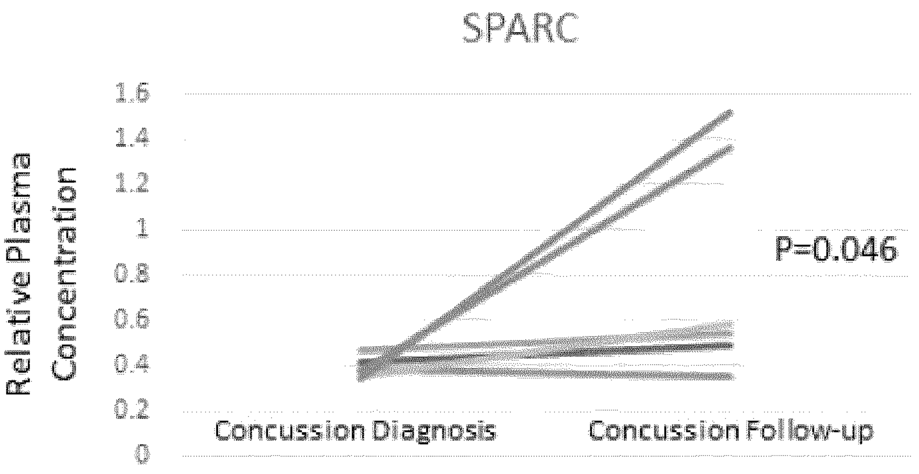
FIGS. 2A-2C: Line graphs illustrating the recovery of 3 plasma protein concentrations between first clinic visit (concussion diagnosis) and follow-up clinic (concussion follow-up). Follow-up clinic interval was variable depending on patient symptoms and availability (less than 3 months after injury diagnosis). The average recoveries, or increase in plasma protein concentrations, were statistically significant. 2A, SPARC P=0.046; 2B, CD34 P=0.046; 2C, IGFBPL1 P=0.028.
Figure 2B:
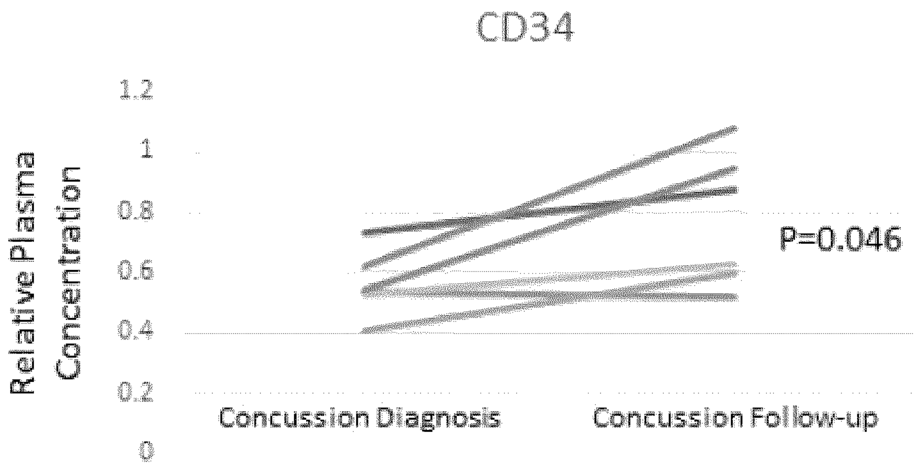
Figure 2C:
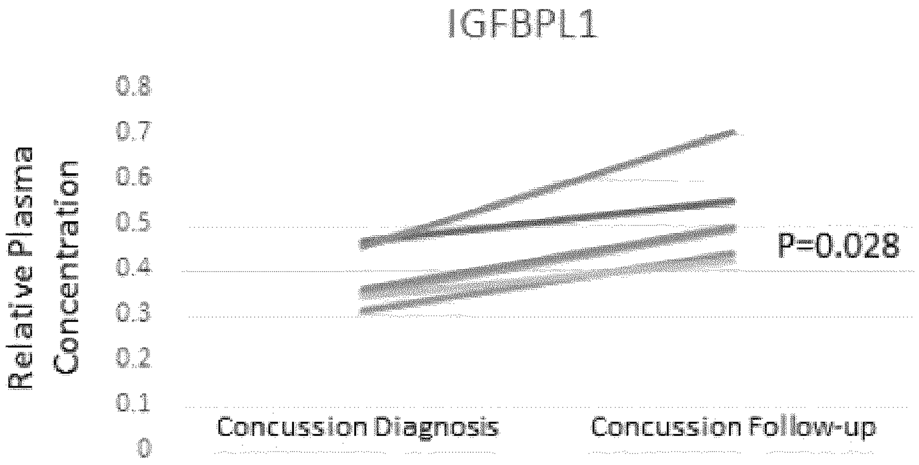

Of the 11 concussion patients, 6 patients agreed to repeat blood work at a follow-up clinic visit. While the timing of the follow-up clinics varied considerably depending on patient symptoms and availability (less than 3 months for all patients), blood was drawn and plasma analyzed with PEA for SPARC, CD34 and IGFBPL1. FIG. 2 illustrates the results from the 6 concussion patients that also had a measurement at follow-up (each line in FIG. 2 represents a patient with 2 measurements, one at concussion diagnosis within 72 hours of injury and the second at a concussion follow-up clinic visit) with regards to measurement of 3 of the top 6 proteins. FIG. 2A is for SPARC, FIG. 2B is for CD34 and FIG. 2C is for IGFBPL1. The measurements suggest that the 3 protein concentrations were significantly recovering with time, albeit unequally and incompletely in each individual patient (SPARC, P=0.046 (FIG. 2A); CD34, P=0.046 (FIG. 2B); and IGFPBL1, P=0.028 (FIG. 2C)). Data are presented as medians (IQRs) with analytes presented as a relative linear concentration.

FIGS. 2A-2C also show recovery of biomarker proteins during the follow up of the patients, which may represent healing. Diagnostic levels could guide frequency and level of rehab, while recovery could guide duration of rehab/therapy and determine when a patient can return to activities safely-sport, school, work and so forth.

TABLE 1

Subject demographics and clinical data.

| | Concussion Patients (n = 11) | Control Subjects (n = 24) | P-value |
|---|---|---|---|
| Age in years | 13.0 (13.0, 14.0) | 13.0 (12.3, 14.0) | 0.406 |
| Sex | 11 M: 0 F | 24 M: 0 F | 1.000 |
| Medical History | | | |
| Concussion(s) | 3 (27) | 6 (25) | 1.000 |
| Anxiety | 1 (9) | 0 | 0.314 |
| Depression | 1 (9) | 0 | 0.314 |
| Mood disorder | 1 (9) | 0 | 0.314 |
| Pre-existing condition | 4 (36) | 3 (13) | 0.171 |
| Medications | 3 (27) | 4 (17) | 0.652 |
| Mechanism of injury | | | |
| Body checked | 4 (36) | — | — |
| Tripped/Fell | 4 (36) | — | — |
| Head into boards | 1 (9) | — | — |
| Elbowed | 1 (9) | — | — |
| Unknown | 1 (9) | — | — |
| Injury Details | | | |
| Loss of consciousness | 1 (9) | — | — |
| Amnesia | 4 (36) | — | — |
| SCAT3 | | | |
| Number of symptoms | 13 (7, 16) | 0 (0, 0) | <0.001 |
| Symptom severity score | 25 (12, 49) | 0 (0, 0) | <0.001 |

Continuous data are presented as medians (IQRs), and categorical data are presented as frequency (percent). SCAT3, Sports Concussion Assessment Tool-3$^{rd}$ Edition.

TABLE 2

Protein concentration comparisons (n = 92) between concussion patients and control subjects.

| Protein | Concussion Patients (n = 11) | Control Subjects (n = 24) | P-value | AUC |
|---|---|---|---|---|
| ATOX1 | 0.50 (0.47, 0.52) | 0.57 (0.52, 0.73) | 0.003 | 0.814 |
| SPARC | 0.41 (0.35, 0.55) | 0.65 (0.50, 0.80) | 0.004 | 0.811 |
| CD34 | 0.55 (0.53, 0.62) | 0.69 (0.62, 0.84) | 0.006 | 0.792 |
| PQBP1 | 0.47 (0.40, 0.62) | 0.64 (0.54, 0.82) | 0.008 | 0.784 |
| IGFBPL1 | 0.43 (0.35, 0.46) | 0.48 (0.44, 0.55) | 0.008 | 0.784 |
| NT5C3A | 0.98 (0.91, 1.26) | 0.75 (0.59, 0.91) | 0.009 | 0.780 |
| COL4A1 | 0.39 (0.34, 0.49) | 0.55 (0.44, 0.66) | 0.009 | 0.777 |
| SPINT2 | 0.43 (0.41, 0.44) | 0.35 (0.33, 0.42) | 0.009 | 0.777 |
| CRTAC1 | 0.17 (0.13, 0.22) | 0.22 (0.21, 0.31) | 0.011 | 0.773 |
| S100P | 0.55 (0.48, 0.70) | 0.71 (0.64, 0.88) | 0.011 | 0.773 |
| HAVCR1 | 0.16 (0.12, 0.20) | 0.11 (0.09, 0.15) | 0.012 | 0.769 |
| APBB1IP | 0.46 (0.37, 0.53) | 0.54 (0.46, 0.60) | 0.013 | 0.765 |
| KYNU | 0.26 (0.18, 0.30) | 0.32 (0.26, 0.40) | 0.013 | 0.765 |
| SPINK6 | 0.25 (0.14, 0.26) | 0.32 (0.21, 0.50) | 0.014 | 0.761 |
| JUN | 0.42 (0.38, 0.44) | 0.47 (0.41, 0.60) | 0.014 | 0.761 |
| TRIM5 | 0.76 (0.70, 0.87) | 0.92 (0.81, 1.07) | 0.014 | 0.761 |
| PPP3R1 | 0.54 (0.44, 0.59) | 0.66 (0.57, 0.71) | 0.016 | 0.758 |
| IL6 | 0.41 (0.32, 0.51) | 0.58 (0.44, 0.99) | 0.016 | 0.758 |
| BAIAP2 | 0.40 (0.30, 0.55) | 0.53 (0.45, 0.80) | 0.016 | 0.758 |
| MPO | 0.30 (0.27, 0.37) | 0.37 (0.34, 0.44) | 0.017 | 0.754 |
| ANKRD54 | 0.81 (0.67, 0.92) | 0.63 (0.58, 0.75) | 0.017 | 0.754 |
| MSTN | 0.30 (0.22, 0.31) | 0.41 (0.29, 0.52) | 0.017 | 0.754 |
| DRAXIN | 0.82 (0.74, 1.09) | 1.25 (0.95, 1.46) | 0.019 | 0.750 |
| CDH2 | 0.23 (0.20, 0.26) | 0.28 (0.24, 0.34) | 0.019 | 0.750 |
| PLA2G10 | 0.47 (0.38, 0.65) | 0.72 (0.52, 0.86) | 0.021 | 0.746 |
| LAMP2 | 0.49 (0.44, 0.54) | 0.57 (0.48, 0.71) | 0.021 | 0.746 |
| HSPB6 | 0.13 (0.12, 0.16) | 0.19 (0.14, 0.25) | 0.021 | 0.746 |
| WIF1 | 0.73 (0.56, 0.89) | 0.95 (0.80, 1.07) | 0.021 | 0.746 |
| PPY | 0.13 (0.11, 0.15) | 0.18 (0.13, 0.27) | 0.021 | 0.746 |
| L1CAM | 0.56 (0.50, 0.56) | 0.63 (0.52, 0.67) | 0.021 | 0.746 |
| PON2 | 0.61 (0.51, 0.70) | 0.76 (0.60, 0.84) | 0.021 | 0.746 |
| EDIL3 | 0.89 (0.85, 0.96) | 1.11 (0.86, 1.38) | 0.021 | 0.746 |
| SPINK4 | 0.48 (0.44, 0.57) | 0.64 (0.50, 0.78) | 0.021 | 0.746 |
| IL16 | 0.18 (0.17, 0.23) | 0.25 (0.19, 0.31) | 0.021 | 0.746 |
| CXCL8 | 0.41 (0.33, 0.58) | 0.31 (0.27, 0.38) | 0.023 | 0.742 |
| CPE | 0.34 (0.29, 0.38) | 0.43 (0.33, 0.53) | 0.023 | 0.742 |
| ADA2 | 0.40 (0.37, 0.48) | 0.51 (0.43, 0.59) | 0.023 | 0.742 |
| EPHA1 | 0.27 (0.23, 0.34) | 0.22 (0.15, 0.28) | 0.023 | 0.742 |
| EPO | 0.35 (0.30, 0.37) | 0.41 (0.34, 0.49) | 0.023 | 0.742 |
| LIF | 0.51 (0.45, 0.62) | 0.62 (0.56, 0.70) | 0.025 | 0.739 |
| LBR | 0.46 (0.40, 0.48) | 0.53 (0.46, 0.57) | 0.025 | 0.739 |
| SETMAR | 0.34 (0.32, 0.39) | 0.41 (0.35, 0.46) | 0.025 | 0.739 |
| SCLY | 0.27 (0.23, 0.33) | 0.35 (0.29, 0.39) | 0.025 | 0.739 |
| CD209 | 0.17 (0.16, 0.22) | 0.23 (0.20, 0.31) | 0.025 | 0.739 |
| FBP1 | 0.28 (0.24, 0.32) | 0.39 (0.31, 0.55) | 0.025 | 0.739 |
| TMSB10 | 0.20 (0.18, 0.21) | 0.28 (0.19, 0.33) | 0.028 | 0.735 |
| FCRL5 | 0.31 (0.27, 0.39) | 0.25 (0.22, 0.33) | 0.030 | 0.731 |
| RHOC | 0.42 (0.37, 0.45) | 0.47 (0.41, 0.58) | 0.030 | 0.731 |
| ATP6V1D | 1.15 (1.06, 1.31) | 1.02 (0.98, 1.15) | 0.030 | 0.731 |
| TGM2 | 2.83 (2.02, 5.00) | 2.13 (1.70, 2.97) | 0.030 | 0.731 |
| CCN2 | 0.45 (0.39, 0.57) | 0.54 (0.47, 0.66) | 0.030 | 0.731 |
| SCGB3A2 | 0.27 (0.18, 0.32) | 0.34 (0.28, 0.49) | 0.030 | 0.731 |
| HNMT | 0.17 (0.16, 0.19) | 0.23 (0.17, 0.30) | 0.033 | 0.727 |
| TNXB | 0.58 (0.51, 0.68) | 0.70 (0.60, 0.79) | 0.033 | 0.727 |
| TXNDC5 | 0.48 (0.41, 0.57) | 0.55 (0.48, 0.68) | 0.033 | 0.727 |
| SMOC1 | 0.11 (0.10, 0.13) | 0.14 (0.12, 0.17) | 0.033 | 0.727 |
| FMR1 | 0.82 (0.65, 0.90) | 0.96 (0.84, 1.06) | 0.033 | 0.727 |
| RABEPK | 0.83 (0.66, 0.95) | 1.01 (0.81, 1.06) | 0.033 | 0.727 |
| LPL | 0.62 (0.48, 0.80) | 0.77 (0.64, 0.91) | 0.033 | 0.727 |
| DNMBP | 0.30 (0.26, 0.33) | 0.36 (0.32, 0.44) | 0.036 | 0.723 |
| SNCG | 0.16 (0.14, 0.19) | 0.23 (0.17, 0.33) | 0.036 | 0.723 |
| CNTN5 | 0.57 (0.45, 0.63) | 0.76 (0.53, 1.05) | 0.036 | 0.723 |
| CDH15 | 0.45 (0.42, 0.62) | 0.60 (0.46, 0.81) | 0.036 | 0.723 |
| EPS8L2 | 0.29 (0.28, 0.33) | 0.40 (0.28, 0.47) | 0.036 | 0.723 |
| CCL14 | 0.55 (0.48, 0.60) | 0.45 (0.38, 0.50) | 0.036 | 0.723 |
| DCTPP1 | 0.36 (0.27, 0.37) | 0.42 (0.34, 0.48) | 0.036 | 0.723 |
| ANGPTL1 | 0.41 (0.39, 0.58) | 0.53 (0.48, 0.67) | 0.036 | 0.723 |
| CLC | 0.35 (0.32, 0.39) | 0.46 (0.36, 0.55) | 0.036 | 0.723 |
| IL12B | 0.60 (0.54, 0.67) | 0.75 (0.58, 0.86) | 0.036 | 0.723 |
| RAB6A | 0.33 (0.27, 0.39) | 0.40 (0.33, 0.49) | 0.036 | 0.723 |
| CLEC4A | 0.43 (0.38, 0.55) | 0.58 (0.47, 0.73) | 0.036 | 0.723 |
| CLEC11A | 0.58 (0.47, 0.64) | 0.73 (0.56, 0.90) | 0.039 | 0.720 |
| FABP5 | 0.31 (0.25, 0.34) | 0.37 (0.32, 0.43) | 0.039 | 0.720 |

TABLE 2-continued

Protein concentration comparisons (n = 92) between concussion patients and control subjects.

| Protein | Concussion Patients (n = 11) | Control Subjects (n = 24) | P-value | AUC |
|---|---|---|---|---|
| LYPD1 | 1.06 (0.89, 1.14) | 1.13 (1.06, 1.32) | 0.039 | 0.720 |
| ANXA3 | 0.20 (0.18, 0.29) | 0.25 (0.23, 0.30) | 0.039 | 0.720 |
| STX16 | 0.64 (0.61, 0.66) | 0.56 (0.45, 0.63) | 0.039 | 0.720 |
| VWF | 0.21 (0.18, 0.34) | 0.30 (0.24, 0.43) | 0.039 | 0.720 |
| PLA2G2A | 0.70 (0.55, 0.96) | 0.92 (0.73, 1.33) | 0.039 | 0.720 |
| NCAM1 | 0.46 (0.41, 0.50) | 0.58 (0.46, 0.64) | 0.039 | 0.720 |
| ATXN10 | 0.12 (0.06, 0.14) | 0.15 (0.12, 0.17) | 0.043 | 0.716 |
| TEK | 0.38 (0.36, 0.44) | 0.44 (0.39, 0.51) | 0.043 | 0.716 |
| CES2 | 0.43 (0.39, 0.49) | 0.34 (0.30, 0.44) | 0.043 | 0.716 |
| CLEC1A | 0.62 (0.56, 0.76) | 0.76 (0.68, 0.91) | 0.043 | 0.716 |
| NUDC | 0.35 (0.32, 0.38) | 0.41 (0.36, 0.52) | 0.043 | 0.716 |
| FST | 0.18 (0.11, 0.21) | 0.24 (0.16, 0.27) | 0.043 | 0.716 |
| NEFL | 0.44 (0.39, 0.55) | 0.37 (0.29, 0.43) | 0.047 | 0.712 |
| ENO2 | 0.78 (0.70, 0.84) | 0.87 (0.79, 0.95) | 0.047 | 0.712 |
| NOS1 | 0.09 (0.06, 0.13) | 0.12 (0.09, 0.15) | 0.047 | 0.712 |
| MIA | 0.71 (0.53, 0.80) | 0.79 (0.67, 0.93) | 0.047 | 0.712 |
| ACTA2 | 0.44 (0.40, 0.51) | 0.54 (0.46, 0.67) | 0.047 | 0.712 |
| TYMP | 0.26 (0.25, 0.33) | 0.35 (0.27, 0.41) | 0.047 | 0.712 |
| SDC1 | 0.46 (0.37, 0.56) | 0.35 (0.32, 0.44) | 0.047 | 0.712 |

Data are presented as median (IQRs).
AUC, area under the curve.

REFERENCES 1. http://www.cdc.gov/TraumaticBraininjury.
2. Bakhos, L. L., Lockhart, G. R., Myers, R. and Linakis, J. G. (2010). Emergency department visits for concussion in young child athletes. Pediatrics. 126, e550-556.
3. Stewart, T. C., Gilliland, J. and Fraser, D. D. (2014). An epidemiologic profile of pediatric concussions: identifying urban and rural differences. J Trauma Acute Care Surg. 76,736-742.
4. McCrory, P., Meeuwisse, W., Dvorak, J., Aubry, M., Bailes, J., Broglio, S., Cantu, R. C., Cassidy, D., Echemendia, R. J., Castellani, R. J., Davis, G. A., Ellenbogen, R., Emery, C., Engebretsen, L., Feddermann-Demont, N., Giza, C. C., Guskiewicz, K. M., Herring, S., Iverson, G. L., Johnston, K. M., Kissick, J., Kutcher, J., Leddy, J. J., Maddocks, D., Makdissi, M., Manley, G. T., McCrea, M., Meehan, W. P., Nagahiro, S., Patricios, J., Putukian, M., Schneider, K. J., Sills, A., Tator, C. H., Turner, M. and Vos, P. E. (2017). Consensus statement on concussion in sport—the 5(th) international conference on concussion in sport held in Berlin, October 2016. Br J Sports Med. 51,838-847.
5. Asken, B. M., Snyder, A. R., Smith, M. S., Zaremski, J. L. and Bauer, R. M. (2017). Concussion-like symptom reporting in non-concussed adolescent athletes. Clin Neuropsychol. 31,138-153.
6. Smith-Seemiller, L., Fow, N. R., Kant, R. and Franzen, M. D. (2003). Presence of post-concussion syndrome symptoms in patients with chronic pain vs mild traumatic brain injury. Brain Inj. 17,199-206.
7. Karlin, A. M. (2011). Concussion in the pediatric and adolescent population: "different population, different concerns". P M R. 3, S369-379.
8. Patel, D. R. and Reddy, V. (2010). Sport-related concussion in adolescents. Pediatr Clin North Am. 57,649-670.
9. Babl, F. E., Dionisio, D., Davenport, L., Baylis, A., Hearps, S. J. C., Bressan, S., Thompson, E. J., Anderson, V., Oakley, E. and Davis, G. A. (2017). Accuracy of Components of SCAT to Identify Children With Concussion. Pediatrics. 140.

10. Harriss, A. B., Abbott, K. C., Humphreys, D., Daley, M., Moir, M. E., Woehrle, E., Balestrini, C. S., Fischer, L. K., Fraser, D. D. and Shoemaker, J. K. (2019). Concussion Symptoms Predictive of Adolescent Sport-Related Concussion Injury. Clin J Sport Med.
11. Kim, H. J., Tsao, J. W. and Stanfill, A. G. (2018). The current state of biomarkers of mild traumatic brain injury. JCI Insight. 3.
12. Mannix, R., Levy, R., Zemek, R., Yeates, K. O., Arbogast, K., Meehan, W. P., Leddy, J., Master, C., Mayer, A. R., Howell, D. R. and Meier, T. B. (2020). Fluid Biomarkers of Pediatric Mild Traumatic Brain Injury: A Systematic Review. J Neurotrauma. 37,2029-2044.
13. Miller, M. R., Robinson, M., Bartha, R., Charyk Stewart, T., Fischer, L., Dekaban, G., Menon, R. S., Shoemaker, J. K. and Fraser, D. D. (2020). Concussion acutely decreases plasma glycerophospholipids in adolescent male athletes. J Neurotrauma. In reviw.
14. Daley, M., Dekaban, G., Bartha, R., Brown, A., Stewart, T. C., Doherty, T., Fischer, L., Holmes, J., Menon, R. S., Rupar, C. A., Shoemaker, J. K. and Fraser, D. D. (2016). Metabolomics profiling of concussion in adolescent male hockey players: a novel diagnostic method. Metabolomics. 12,185.
15. Lumba-Brown, A., Yeates, K. O., Sarmiento, K., Breiding, M. J., Haegerich, T. M., Gioia, G. A., Turner, M., Benzel, E. C., Suskauer, S. J., Giza, C. C., Joseph, M., Broomand, C., Weissman, B., Gordon, W., Wright, D. W., Moser, R. S., McAvoy, K., Ewing-Cobbs, L., Duhaime, A. C., Putukian, M., Holshouser, B., Paulk, D., Wade, S. L., Herring, S. A., Halstead, M., Keenan, H. T., Choe, M., Christian, C. W., Guskiewicz, K., Raksin, P. B., Gregory, A., Mucha, A., Taylor, H. G., Callahan, J. M., DeWitt, J., Collins, M. W., Kirkwood, M. W., Ragheb, J., Ellenbogen, R. G., Spinks, T. J., Ganiats, T. G., Sabelhaus, L. J., Altenhofen, K., Hoffman, R., Getchius, T., Gronseth, G., Donnell, Z., O'Connor, R. E. and Timmons, S. D. (2018). Centers for Disease Control and Prevention Guideline on the Diagnosis and Management of Mild Traumatic Brain Injury Among Children. JAMA Pediatr. 172, e182853.
16. Greenwood, C., Ruff, D., Kirvell, S., Johnson, G., Dhillon, H. S. and Bustin, S. A. (2015). Proximity assays for sensitive quantification of proteins. Biomol Detect Quantif. 4,10-16.
17. Assarsson, E., Lundberg, M., Holmquist, G., Bjorkesten, J., Thorsen, S. B., Ekman, D., Eriksson, A., Rennel Dickens, E., Ohlsson, S., Edfeldt, G., Andersson, A. C., Lindstedt, P., Stenvang, J., Gullberg, M. and Fredriksson, S. (2014). Homogenous 96-plex PEA immunoassay exhibiting high sensitivity, specificity, and excellent scalability. PLOS One. 9, e95192.
18. Guskiewicz, K. M., Register-Mihalik, J., McCrory, P., McCrea, M., Johnston, K., Makdissi, M., Dvorak, J., Davis, G. and Meeuwisse, W. (2013). Evidence-based approach to revising the SCAT2: introducing the SCAT3. Br J Sports Med. 47,289-293.
19. Zhu, W., Zeng, N. and Wang, N. (2010). Sensitivity, Specificity, Accuracy, Associated Confidence Interval and ROC Analysis with Practical SAS® Implementations. Northeast SAS Users Group Proceedings. http://www.lexjansen.com/nesug/nesu@10/hl/hl07.pdf.
20. Cusimano, M. D., Topolovec-Vranic, J., Zhang, S., Mullen, S. J., Wong, M. and Ilie, G. (2017). Factors Influencing the Underreporting of Concussion in Sports: A Qualitative Study of Minor Hockey Participants. Clin J Sport Med. 27,375-380.
21. Meier, T. B., Brummel, B. J., Singh, R., Nerio, C. J., Polanski, D. W. and Bellgowan, P. S. (2015). The underreporting of self-reported symptoms following sports-related concussion. J Sci Med Sport. 18,507-511.
22. McCrory, P., Meeuwisse, W., Aubry, M., Cantu, B., Dvorak, J., Echemendia, R. J., Engebretsen, L., Johnston, K., Kutcher, J. S., Raftery, M., Sills, A., Kathryn Schneider, P. T. P. C. H. T. M. D. P. H. D., Benson, B. W., Davis, G. A., Ellenbogen, R. G., Guskiewicz, K. M., Herring, S. A., Iverson, G., Jordan, B. D., Kissick, J., McCrea, M., McIntosh, A. S., Maddocks, D. L., Makdissi, M., Purcell, L., Putukian, M., Turner, M., Schneider, K. and Tator, C. H. (2013). Consensus statement on concussion in sport—the 4th International Conference on Concussion in Sport held in Zurich, November 2012. Clin J Sport Med. 23,89-117.
23. Mclendon, L. A., Kralik, S. F., Grayson, P. A. and Golomb, M. R. (2016). The Controversial Second Impact Syndrome: A Review of the Literature. Pediatr Neurol. 62,9-17.
24. Manning, K. Y., Schranz, A., Bartha, R., Dekaban, G. A., Barreira, C., Brown, A., Fischer, L., Asem, K., Doherty, T. J., Fraser, D. D., Holmes, J. and Menon, R. S. (2017). Multiparametric MRI changes persist beyond recovery in concussed adolescent hockey players. Neurology. 89,2157-2166.
25. McCrea, M., Broglio, S. P., McAllister, T. W., Gill, J., Giza, C. C., Huber, D. L., Harezlak, J., Cameron, K. L., Houston, M. N., McGinty, G., Jackson, J. C., Guskiewicz, K., Mihalik, J., Brooks, M. A., Duma, S., Rowson, S., Nelson, L. D., Pasquina, P., Meier, T. B., and the, C. C. I., Foroud, T., Katz, B. P., Saykin, A. J., Campbell, D. E., Svoboda, S. J., Goldman, J. and DiFiori, J. (2020). Association of Blood Biomarkers With Acute Sport-Related Concussion in Collegiate Athletes: Findings From the NCAA and Department of Defense CARE Consortium. JAMA Netw Open. 3, e1919771.
26. Jacquin, A., Kanakia, S., Oberly, D. and Prichep, L. S. (2018). A multimodal biomarker for concussion identification, prognosis and management. Comput Biol Med. 102,95-103.
27. Hasan, K. M., Keser, Z., Schulz, P. E. and Wilde, E. A. (2018). Multimodal Advanced Imaging for Concussion. Neuroimaging Clin N Am. 28,31-42.
28. Keightley, M., Green, S., Reed, N., Agnihotri, S., Wilkinson, A. and Lobaugh, N. (2011). An investigation of the effects of sports-related concussion in youth using functional magnetic resonance imaging and the head impact telemetry system. J Vis Exp.
29. Ransom, D. M., Burns, A. R., Youngstrom, E. A., Vaughan, C. G., Sady, M. D. and Gioia, G. A. (2016). Applying an Evidence-Based Assessment Model to Identify Students at Risk for Perceived Academic Problems following Concussion. J Int Neuropsychol Soc. 22,1038-1049.
30. Howell, D. R., Myer, G. D., Brilliant, A., Barber Foss, K. and Meehan, W. P., 3rd. (2019). Quantitative Multimodal Assessment of Concussion Recovery in Youth Athletes. Clin J Sport Med.
31. Rosenfeld, et al., Lancet Neurol. 2013 September;12 (9): 882-93.

Through the embodiments that are illustrated and described, the currently contemplated best mode of making and using the invention is described. Without further elaboration, it is believed that one of ordinary skill in the art can, based on the description presented herein, utilize the present invention to the full extent. All publications cited herein are incorporated by reference.

Although the description above contains many specificities, these should not be construed as limiting the scope of the invention, but as merely providing illustrations of some of the presently embodiments of this invention.

What is claimed is:

1. A method of diagnosing an acquired central nervous system injury in a subject comprising: (a) obtaining a biological sample from the subject and measuring levels of a biomarker in the biological sample, (b) comparing the levels of the biomarker in the biological sample with control reference levels of the biomarker, wherein a change in the levels of the biomarker in the biological sample relative to the control reference levels of the biomarker is indicative of a positive acquired central nervous system injury diagnosis in the subject, the biomarker being one or combination of two or more of ATOX1, SPARC, CD34, PQBP1, IGFBPL1 and/or NT5C3A, wherein the levels of ATOX1, SPARC, CD34, PQBP1 and IGFBPL1 are decreased in the biological sample relative to the control reference levels, and the level of NT5C3A is increased in the biological sample relative to the control reference level, and (c) administering to the subject an agent effective for the treatment of acquired central nervous system injury only when there is a change in the levels of the biomarker in the biological sample relative to the control reference levels of the biomarker indicative of the positive acquired central nervous system injury diagnosis of the subject.

2. The method of claim 1, wherein the biomarker is a combination of ATOX1 and SPARC, or a combination of ATOX1, SPARC and NT5C3A.

3. The method of claim 1, wherein the method further comprises obtaining recovery samples from the subject during the subject's treatment for acquired central nervous system injury and measuring levels of the biomarker in the recovery samples, wherein an approximation in the levels of the biomarker in the recovery samples to the control reference levels is indicative of a normalization of the subject.

4. The method of claim 1, wherein the control reference levels of the biomarker are derived from normal subjects or from acquired central nervous system injury positive subjects.

5. The method of claim 1, wherein the biomarker is selected based on an area under the curve receiver operating characteristic analysis of the biomarker.

6. The method of claim 5, wherein the area under the curve of the biomarker is 0.78 or more.

7. The method of claim 1, wherein the biological sample is blood, blood plasma, blood serum, capillary blood, saliva, tear, sweat, synovial fluid, urine, spinal fluid, bronchoalveolar lavage, hippocampal tissue or ipsilateral cortex tissue and extracts.

8. The method of claim 1, wherein the acquired central nervous system injury is mild traumatic brain injury, non-traumatic brain injury, mild traumatic spinal cord injury or non-traumatic spinal cord injury.

9. The method of claim 1, wherein the acquired central nervous system injury is concussion or blast-induced traumatic brain injury.

10. A method of treating acquired central nervous system injury in a subject, the method comprising administering to the subject an inhibitor or antagonist of NT5C3A and/or administering to the subject one or a combination of, SPARC, CD34, PQBP1, IGFBPL1, or their fragments, agonists or analogues.

11. The method of claim 10, wherein the acquired central nervous system injury is mild traumatic brain injury, non-traumatic brain injury, mild traumatic spinal cord injury or non-traumatic spinal cord injury.

12. The method of claim 10, wherein the acquired central nervous system injury is concussion or blast-induced traumatic brain injury.

13. An acquired central nervous system injury diagnostic apparatus, the acquired central nervous system injury diagnostic apparatus including a non-transitory computer readable storage medium storing computer-executable instructions that when executed by a computer control the computer for performing a method of diagnosing acquired central nervous system injury in a subject, said executable instructions comprising: (a) comparing levels of a biomarker in a biological sample of the subject, with control reference levels of the biomarker, and (b) providing an acquired central nervous system injury positive signal when there is a change in the levels of the biomarker the biological sample relative to the control reference levels of the biomarker, the biomarker being one or a combination of two or more of ATOX1, SPARC, CD34, PQBP1, IGFBPL1 and/or NT5C3A and wherein the levels of ATOX1, SPARK, CD34, PQBP1 and IGFBPL1 are decreased in the biological sample relative to the control reference levels, and the level of NT5C3A is increased in the biological sample relative to the control reference level.

14. The acquired central nervous system injury diagnostic apparatus of claim 13, wherein the biomarker is a combination of ATOX1 and SPARC or a combination of ATOX1, SPARC and NT5C3A.

15. The acquired central nervous system injury ACNSI diagnostic apparatus of claim 13, wherein the instructions further include comparing the levels of the biomarker in the biological sample, with the levels of the biomarker in a sample obtained from the subject during treatment of the subject for acquired central nervous system injury, wherein an approximation to the control reference levels of said biomarker is indicative of a normalization of the subject.

16. The acquired central nervous system injury diagnostic apparatus of claim 13, wherein the biological sample is blood, blood plasma, blood serum, capillary blood, saliva, tear, sweat, synovial fluid, urine, spinal fluid, bronchoalveolar lavage, hippocampal tissue or ipsilateral cortex tissue and extracts.

17. The acquired central nervous system injury diagnostic apparatus of claim 13, wherein the acquired central nervous system injury is mild traumatic brain injury, non-traumatic brain injury, mild traumatic spinal cord injury or non-traumatic spinal cord injury.

18. The acquired central nervous system injury diagnostic apparatus of claim 13, wherein the acquired central nervous system injury is concussion or blast-induced traumatic brain injury.

* * * * *